United States Patent [19]
Sullivan et al.

[11] 3,939,379
[45] Feb. 17, 1976

[54] HIGH ENERGY GAS DISCHARGE SWITCHING DEVICE

[75] Inventors: John W. Sullivan, Los Altos; Richard P. Fleenor, Los Gatos, both of Calif.

[73] Assignee: Gould Inc., Chicago, Ill.

[22] Filed: Feb. 18, 1975

[21] Appl. No.: 550,300

Related U.S. Application Data

[63] Continuation of Ser. No. 483,114, June 26, 1974, abandoned.

[52] U.S. Cl. .............. 315/85; 313/201; 313/206; 313/219; 313/313; 315/330; 315/335
[51] Int. Cl.² .... H01J 1/52; H01J 5/02; H01J 11/04
[58] Field of Search .......... 313/198, 201, 206, 219, 313/234, 239, 242, 313, 326, 356; 315/85, 330, 335, 338, 344

[56] References Cited
UNITED STATES PATENTS

| | | | |
|---|---|---|---|
| 2,313,646 | 3/1943 | Johnson | 313/201 X |
| 2,478,907 | 8/1949 | Edgerton | 315/261 |
| 2,532,188 | 11/1958 | Penning et al. | 313/313 X |
| 3,723,887 | 3/1973 | Panico | 315/362 X |
| 3,758,819 | 9/1973 | Goldberg | 315/330 X |
| 3,773,050 | 11/1973 | Panico | 128/419 D |
| 3,775,641 | 11/1973 | Goldberg | 315/335 X |

FOREIGN PATENTS OR APPLICATIONS

861,198 2/1941 France

OTHER PUBLICATIONS

Dittmar et al., Ein Transportabler, Etc., Article in "Medizinicher Welt," Apr. 25, 1964, pp. 958–963.

*Primary Examiner*—Archie R. Borchelt
*Assistant Examiner*—E. R. La Roche
*Attorney, Agent, or Firm*—Flehr, Hohbach, Test, Albritton & Herbert

[57] ABSTRACT

High energy switching device utilizing a gas discharge tube with input and output electrodes connected electrically in series with a source and a load. A control element is connected to the input electrode, and a trigger signal is applied to the control element to initiate firing of the tube to pass energy from the source to the load. An electrostatic shield is disposed about the output electrode to prevent the tube from self firing in the absence of a trigger signal when the potential between the electrodes is below a predetermined level.

19 Claims, 4 Drawing Figures

HIGH ENERGY GAS DISCHARGE SWITCHING DEVICE

This is a continuation, of application Ser. No. 483,114 filed June 26, 1974, now abandoned.

BACKGROUND OF THE INVENTION

This invention pertains generally to high energy switching devices and more particularly to high energy switching devices utilizing gas discharge tubes.

Heretofore, Xenon flash tubes and other gas discharge tubes have been utilized for switching large amounts of power by connecting the electrodes of the tube electrically in series with a source and load and applying a trigger pulse to a control terminal to break down the gas and initiate the main discharge to transfer energy from the source to the load. Such switches willl handle voltages on the order of 10KV and currents on the order of several hundred amperes, and they can be switched at very high speeds.

In the past, high energy switches utilizing gas discharge tubes have had a serious limitation in that the tubes have erratic hold-off potentials which typically range from less than 8KV to more than 25KV. Consequently, if the source voltages is 8KV or more, the device may fire by itself, and this self-firing cannot be tolerated in many applications, for example, defibrillators where the device is used to control the application of a defibrillating pulse to a patient's heart.

SUMMARY AND OBJECTS OF THE INVENTION

In the high energy switching device of the invention, an electrostatic shield is placed about the output electrode of the gas discharge tube. It has been observed that this shield results in a highly reliable hold-off potential on the order of 15KV with Xenon flash tubes which are available commercially.

It is in general an object of the invention to provide a new and improved high energy switching device.

Another object of the invention is to provide a switching device of the above character which has a highly reliable hold-off potential and is suitable for use in a defibrillator.

Another objects of the invention is to provide a switching device of the above character which is fail safe in operation.

Additional objects and features of the invention will be apparent from the following description in which the preferred embodiment is set forth in detail in conjunction with the accompanying drawings.

DESCRIPTION OF THE PREFERRED EMBODIMENT

Figure 1:
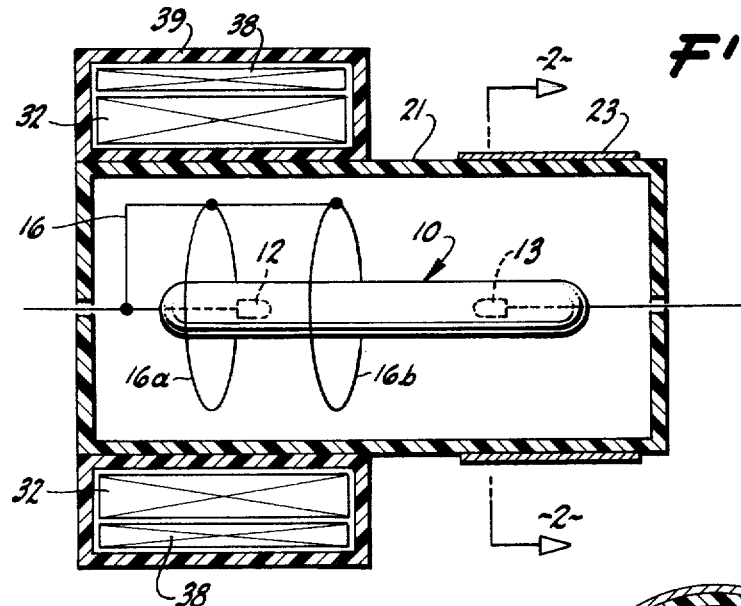
FIG. 1 is a vertical sectional view of one embodiment of a high energy switching device according to the invention.
Figure 2:
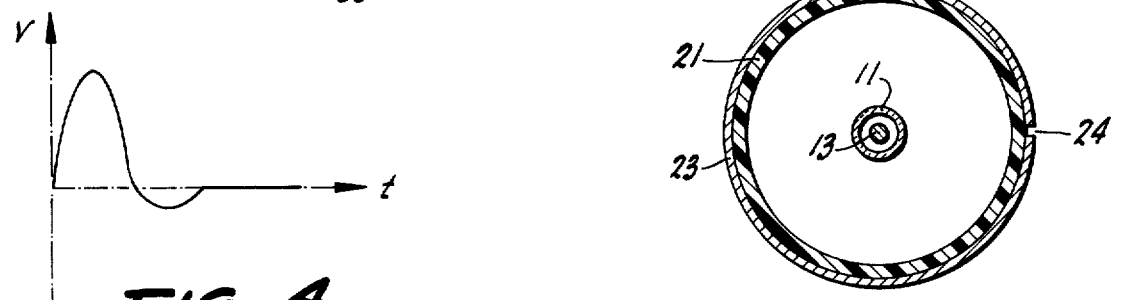
FIG. 2 is a cross-sectional view taken along line 2—2 in FIG. 1.

The switching device includes a gas discharge tube 10 having an elongated glass envelope 11 in which axially spaced electrodes 12 and 13 are enclosed. The envelope is filled with a suitable gas such as Xenon. In the preferred embodiment the tube is a Xenon flash tube, and the pressure within the tube is slightly less than atmospheric pressure, for example.

A trigger element 16 is provided for breaking down the gas in tube 10 and initiating the main discharge between electrodes 12 and 13. The trigger element comprises conductive loops 16a and 16b which are disposed coaxially of the electrodes and connected to electrode 12. The loops are spaced axially apart, with loop 16a adjacent to electrode 12 and loop 16b midway between the electrodes.

Tube 10 and trigger element 16 are enclosed within a generally cylindrical housing 21 fabricated of an electrically insulative material such as plastic. The tube and trigger element are disposed coaxially of the housing and supported by suitable means, not shown. In the preferred embodiment, the tube has a diameter on the order of ¼ to ⅜ inch, the housing has a diameter on the order 1 inch, and loops 16a, 16b are slightly smaller in diameter than the housing.

An electrostatic shield 23 is disposed coaxially about electrode 13. The shield is fabricated of an electrically conductive material, and in the preferred embodiment it consists of a layer of brass foil having a width of 1 inch and a thickness on the order of 0.002 to 0.003 inch wrapped about the end of housing 21 at which electrode 13 is located. The shield is provided with an air gap 24 to prevent it from being a shorted turn. If desired, the shield can be covered by suitable insulating material such as a rubber boot.

Figure 3:
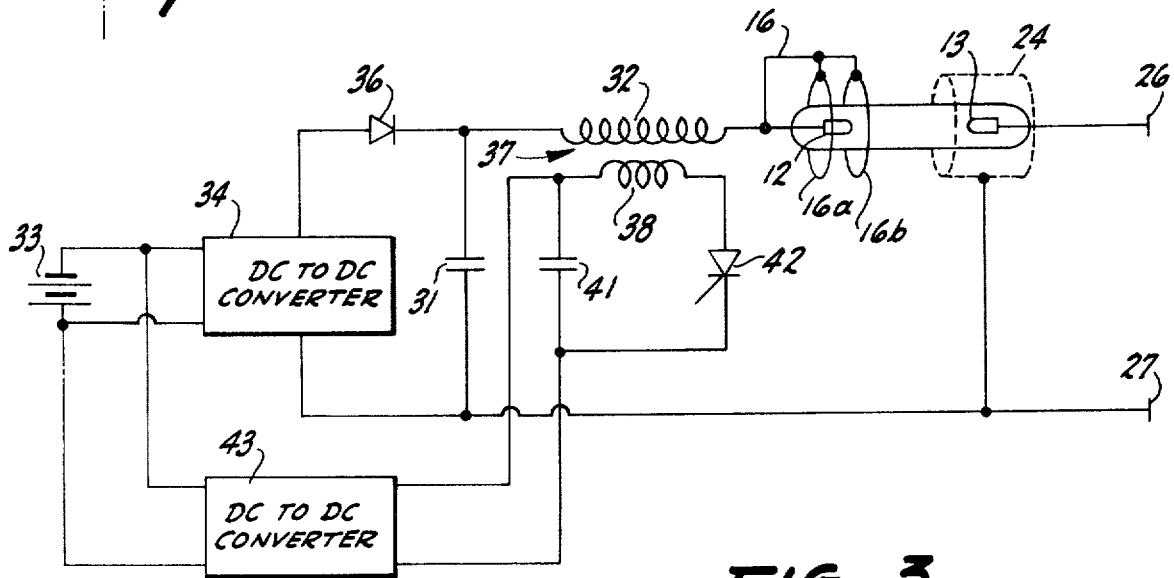
FIG. 3 is a circuit diagram of the switching device of FIG. 1 employed in a defibrillator.

In FIG. 3, the switching device is illustrated in connection with a defibrillator having output terminals or paddles 26, 27 adapted to be placed in contact with a patient's body for delivering a defibrillating pulse to the patient's heart. Paddle 26 is connected to electrode 13, which serves as an output electrode, and paddle 27 is connected to shield 24 and to a capacitor 31.

Capacitor 31 and the secondary winding 32 of a transformer are connected electrically in series between paddle 27 and input electrode 12. Capacitor 31 serves as a storage capacitor for the energy to be delivered to the patient's heart, and it is charged from a 24 volt battery 33 to a level on the order of 3KV to 7KV by a DC-to-DC converter 34 through a diode 36.

Winding 32 is the secondary winding of a transformer 37 which also has a primary winding 38. In the preferred embodiment, primary winding 38 consists of four to five turns of copper sheet, secondary winding 32 consists of several hundred turns of copper wire, and the transformer is enclosed in a cylindrical case 39 and mounted coaxially of housing 21 adjacent to input electrode 12 and trigger element 16.

Means is provided for applying trigger pulses to trigger element 16 through transformer 37. This means includes a capacitor 41 and a silicon controlled rectifier 42 which are connected electrically in series with primary winding 38. Capacitor 41 is charged to a suitable triggering level, such as 200 volts, from battery 33 by a converter 43 similar to converter 34. The gate of SCR 42 is connected to a suitable control device such as a manually operated switch.

Operation and use of the switching device can be described briefly. Capacitor 41 is charged to a level on the order of 200 volts by converter 43 when the unit is turned on. When converter 34 is energized, capacitor 31 is charged to a level on the order of 3KV to 7KV. Paddles 26 and 27 are placed in contact with the patient's s body, and SCR 42 is fired when a defibrillating pulse is desired. When the SCR fires, capacitor 41 discharges through primary winding 38, producing a trigger pulse on the order of 25KV and 1–2 microseconds duration in secondary winding 32. This pulse ionizes the gas in tube 10, initiating the main discharge between electrodes 12 and 13 to deliver the energy stored in capacitor 41 to paddles 26 and 27.

Figure 4:
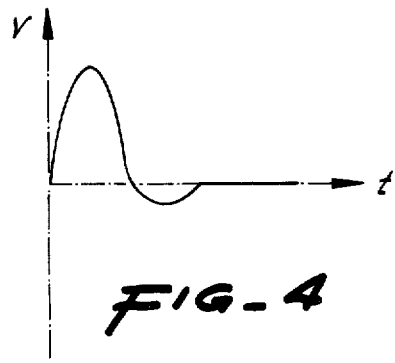
FIG. 4 is a graphical representation of the output voltage produced by the switching device in the circuit of FIG. 3.

Capacitor 31, winding 32 and the patient's body constitute an LCR circuit which produces the waveform shown in FIG. 4 when capacitor 31 discharges. This waveform is commonly known as a Lown waveform, and it is a slightly underdamped sinusoidal waveform which decreases in magnitude at a rate on the order of 82% per half cycle. Tube 10 requires a certain minimum current to sustain ignition, and it extinguishes on the zero crossing at the end of the first or second half cycle of the output voltage, depending on the level to which capacitor 31 is initially charged. With an initial charge of 7KV, for example, the voltage drop at the first zero crossing is very rapid, and the tube does not turn off until the second zero crossing. With a smaller initial charge, e.g. 3KV, the tube extinguishes on the first zero crossing. The pulse delivered to the patient's heart has a duration on the order of 5 to 8 milliseconds and a level depending upon the initial charge on capacitor 31.

It has been found that electrostatic shield 24 is very effective in preventing the discharge tube from firing before the trigger pulse is applied. With the shield, tubes which otherwise would break down with potentials as low as 8KV will consistently and reliably hold off potentials on the order of 15KV. Prior to ignition, the shield is maintained at substantially the same potential as the output electrode and it is believed to perform its function by shaping the electrostatic field in the region of the output electrode and relieving the field gradient concentration which would otherwise occur in this region due to the sharpness of the electrode. This shield has been found to perform its function even when the tube is fired in the presence of external metal objects.

The switching device is fail safe in operation in that it will not fire in the event that the envelope is broken. Trigger element 16 is spaced a substantial distance from electrode 13 and shield 24, and it cannot arc over to either of them in the event the tube should break in such a manner that the electrode 13 is left exposed. In the event of a leak or crack in the envelope, the negative pressure to which the tube is filled will cause the Xenon gas to mix with the incoming air which will cause the hold off voltage to increase.

It is apparent from the foregoing that a new and improved high energy switching device has been provided. While only the preferred embodiment has been described, as will be apparent to those familiar with the art, certain changes and modifications can be made without departing from the scope of the invention as defined by the following claims.

We claim:

1. In a high energy switching device for delivering energy from a source to a load: a gas discharge tube having first and second electrodes connected electrically in series with the source and the load, a control element connected to the first electrode, means for applying a trigger signal to the control element to initiate firing of the tube to pass energy from the source to the load, and means comprising an electrostatic shield disposed about the second electrode for preventing the tube from firing in the absence of a trigger signal when the potential between the electrodes is below a predetermined level.

2. The switching device of claim 1 wherein the gas discharge tube is a Xenon flash tube.

3. The switching device of claim 1 wherein the means for applying the trigger signal comprises a transformer having a secondary winding connected electrically in series with the source and the first electrode.

4. The switching device of claim 1 wherein the pressure within the tube is substantially equal to atmospheric pressure.

5. The switching device of claim 1 wherein the tube includes an elongated envelope, the shield is mounted coaxially of the electrodes toward one end of the envelope, and the control element comprises a pair of conductive loops disposed coaxially of the electrodes toward the second end of the envelope, the loops being of substantially different diameter than the tube.

6. The switching device of claim 1 wherein the source comprises a storage capacitor.

7. The switching device of claim 6 further including a battery and means for delivering a high energy charge to the capacitor from the battery.

8. The switching device of claim 1 wherein the tube comprises an elongated envelope with the electrodes spaced toward opposite ends thereof.

9. The switching device of claim 8 wherein the control element and the electrostatic shield are disposed toward the same ends of the envelope as the electrodes with which they are associated.

10. The switching device of claim 9 wherein the control element comprises a pair of conductive loops disposed coaxially of the electrodes.

11. The switching device of claim 10 wherein one of the control element loops is positioned adjacent to the first electrode and the second loop is positioned between the electrodes.

12. In a device for delivering a high energy pulse to a load connected to a pair of output terminals: a gas discharge tube having an elongated envelope with axially spaced input and output electrodes disposed toward the ends of the envelope, means connecting the output electrode to a first one of the output terminals, a trigger element connected to the input electrode and disposed toward the same end of the envelope as said electrode, an electrostatic shield connected to the second output terminal and disposed coaxially of the output electrode, an energy storage device, means for delivering energy to the storage device, a transformer having primary and secondary windings, means connecting the energy storage device and the secondary winding of the transformer electrically in series with the input electrode and the second output terminal, and means for delivering a trigger pulse to the primary winding of the transformer to initiate firing of the tube to deliver the energy from the storage device to the load connected to the output terminals.

13. The device of claim 12 wherein the gas discharge tube is a Xenon flash tube.

14. The switching device of claim 12 wherein the pressure within the tube is substantially equal to atmospheric pressure.

15. The device of claim 12 wherein the transformer is disposed coaxially about the input electrode.

16. The device of claim 12 wherein the means for delivering the trigger pulse comprises a capacitor and switching means for delivering energy stored in the capacitor to the primary winding.

17. The device of claim 12 wherein the output terminals are defibrillator paddles.

18. The device of claim 12 wherein the energy storage device is a capacitor.

19. The device of claim 18 wherein the means for delivering energy to the capacitor constituting the storage device comprises a battery and a converter powered by the battery for delivering a high voltage charge to the capacitor.

* * * * *